US010603332B2

(12) United States Patent
Sono et al.

(10) Patent No.: US 10,603,332 B2
(45) Date of Patent: Mar. 31, 2020

(54) ANTI-OBESITY COMPOSITION

(71) Applicant: SUNSTAR INC., Osaka (JP)

(72) Inventors: Youko Sono, Osaka (JP); Makoto Suwa, Osaka (JP); Motonobu Matsumoto, Osaka (JP)

(73) Assignee: SUNSTAR INC., Osaka (JP)

( * ) Notice: Subject to any disclaimer, the term of this patent is extended or adjusted under 35 U.S.C. 154(b) by 82 days.

(21) Appl. No.: 15/606,685

(22) Filed: May 26, 2017

(65) Prior Publication Data

US 2017/0258822 A1 Sep. 14, 2017

Related U.S. Application Data

(62) Division of application No. 15/025,324, filed as application No. PCT/JP2014/075809 on Sep. 29, 2014, now abandoned.

(30) Foreign Application Priority Data

Sep. 30, 2013 (JP) ................................. 2013-204110
Sep. 30, 2013 (JP) ................................. 2013-204352

(51) Int. Cl.
A61K 36/00 (2006.01)
A61K 31/7048 (2006.01)
A61K 31/05 (2006.01)
A61K 36/76 (2006.01)
A61K 36/31 (2006.01)
A61K 36/63 (2006.01)
A23L 33/10 (2016.01)
A23L 33/105 (2016.01)
A61K 9/48 (2006.01)
A23L 2/52 (2006.01)
A23G 4/06 (2006.01)
A23G 4/12 (2006.01)
A61K 31/26 (2006.01)
A61P 3/04 (2006.01)
A61K 9/00 (2006.01)
A61K 31/275 (2006.01)
A61K 9/20 (2006.01)

(52) U.S. Cl.
CPC ............ *A61K 31/7048* (2013.01); *A23G 4/06* (2013.01); *A23G 4/068* (2013.01); *A23G 4/12* (2013.01); *A23L 2/52* (2013.01); *A23L 33/10* (2016.08); *A23L 33/105* (2016.08); *A61K 9/0053* (2013.01); *A61K 9/4866* (2013.01); *A61K 31/05* (2013.01); *A61K 31/26* (2013.01); *A61K 31/275* (2013.01); *A61K 36/31* (2013.01); *A61K 36/63* (2013.01); *A61K 36/76* (2013.01); *A61P 3/04* (2018.01); *A61K 9/0095* (2013.01); *A61K 9/2054* (2013.01)

(58) Field of Classification Search
CPC ..................................................... A61K 36/00

USPC ......................................................... 424/725
See application file for complete search history.

(56) References Cited

U.S. PATENT DOCUMENTS

| 2004/0005355 | A1 | 1/2004 | Theoharides |
| 2007/0077317 | A1 | 4/2007 | Theoharides |
| 2009/0061031 | A1* | 3/2009 | Lee-Huang ............ A61K 31/05 424/774 |
| 2012/0201903 | A1 | 8/2012 | Bowman |

FOREIGN PATENT DOCUMENTS

| CN | 102755306 | 10/2012 |
| EP | 2 481 298 | 8/2012 |
| FR | 2792831 | 11/2000 |
| JP | 2002-543103 | 12/2002 |
| JP | 2006-151909 | 6/2006 |
| JP | 2007-119430 | 5/2007 |
| JP | 2013-209351 | 10/2013 |
| KR | 10-2012-0061016 | 6/2012 |
| RU | 2 286 679 | 11/2006 |
| WO | 99/48385 | 9/1999 |
| WO | 00/66078 | 11/2000 |
| WO | 2012/125772 | 9/2012 |

OTHER PUBLICATIONS

Riadh et al., "Oleuropein and hydroxytyrosol inhibit adipocyte differentiation in 3 T3-L1 cells", Life Science, vol. 89, No. 19-20, pp. 708-716 (2011).
Choi et al., "Sulforaphane Inhibits Mitotic Clonal Expansion During Adipogenesis Through Cell Cycle Arrest", Obesity, vol. 20, No. 7, pp. 1365-1371 (2012).
Lee et al., "Salicortin-Derivatives from *Salix Pseudo-lasiogyne* Twigs Inhibit Adipogenesis in 3T3-L1 Cells via Modulation of C/EBPα and SREBP1c Dependent Pathway", Molecules, vol. 18, pp. 10484-10496 (2013).
Office Action dated Feb. 9, 2018 in Chinese Application No. 201480053163.4, with English Translation.
Journal of Physical Fitness, Nutrition and Immunology, 22(3): 235-236 (2012).
Therapeutic Research, 28(10): 1918-1919 (2007).
Hur et al., "Oleuropein reduces free fatty acid-induced lipogenesis via lowered extracellular signal-regulated kinase activation in hepatocytes", Nutrition Research, 32: 778-786 (2012).

(Continued)

*Primary Examiner* — Michael V Meller
(74) *Attorney, Agent, or Firm* — Wenderoth, Lind & Ponack, L.L.P.

(57) ABSTRACT

A method to suppress obesity, comprising administering to a subject in need thereof an effective amount of a composition comprising the following components (A) and (B): (A) oleuropein; and (B) a sulforaphane compound, wherein the amount of component (A) alone contained in the composition does not result in a fat accumulation-suppressing effect, and the amount of component (B) alone contained in the composition does not result in a fat accumulation-suppressing effect.

6 Claims, No Drawings

(56) References Cited

OTHER PUBLICATIONS

Notification of Reasons for Refusal dated Jun. 12, 2018 in corresponding Japanese Application No. 2015-539409, with English Translation.
International Search Report dated Nov. 11, 2014 in International (PCT) Application No. PCT/JP2014/075809.
Panickar "Effects of dietary polyphenols on neuroregulatory factors and pathways that mediate food intake and energy regulation in obesity", Mol. Nutr. Food Res., vol. 57, No. 1, 2013, pp. 34-47.
Vomhof-DeKrey et al., "The Nrf2-antioxidant response element pathway: a target for regulating energy metabolism", Journal of Nutritional Biochemistry, vol. 23, No. 10., 2012, pp. 1201-1206.
Chanioti et al., "Evaluation of extracts prepared from olive oil by-products using microwave-assisted enzymatic extraction—Effect of encapsulation on the stability of final products", Laboratory of Food Chemistry and Technology, 2015.
Omar, "Oleuropein in Olive and its Pharmacological Effects", Scientia Pharmaceutica, vol. 78, No. 2, 2010, pp. 133-154.
Partial Supplementary European Search Report, dated Apr. 12, 2017, in corresponding European Application No. 14847844.9.

\* cited by examiner

ANTI-OBESITY COMPOSITION

TECHNICAL FIELD

The present invention relates to an obesity-suppressing composition (anti-obesity composition). More specifically, the present invention relates to an obesity-suppressing composition suppressing fat accumulation and comprising oleuropein in combination with one or more members selected from willow extract and sulforaphane.

BACKGROUND ART

Due to lifestyle factors, such as the spread of high-calorie foods and a reduction in daily physical activity, the number of people who develop diabetes or who are insulin resistant is increasing not only in middle-aged and elderly people, but also in young people. One of the main factors for this is obesity. Obesity is a state of excessive body fat. This state is considered to be associated with the hypertrophy of adipocytes themselves and the increased number of adipocytes. Hypertrophied adipocytes are called "hypertrophic adipocytes," which are presumably produced through the accumulation of fat in adipocytes. The production of "hypertrophic adipocytes" may lead to a vicious circle in which fat accumulation in adipocytes newly produced by cell proliferation is promoted, thereby resulting in a significant increase in body weight and a significant change in body shape. Accordingly, the production of "hypertrophic adipocytes" can be suppressed or prevented by suppressing or preventing the accumulation of fat droplets in adipocytes. Consequently, it is possible to prevent a significant increase in body weight and a significant change in body shape.

For example, as a food and pharmaceutical for eliminating and preventing obesity, PTL 1 discloses a composition for suppressing fat accumulation in white adipocytes. This is a composition for internal use comprising α-lipoic acid, coenzyme Q10, and at least one amino acid selected from valine, leucine, and isoleucine.

To suppress or prevent the accumulation of fat droplets in adipocytes by an oral composition, a daily intake of the oral composition is required. Therefore, it is desirable to use highly safe, naturally occurring components.

CITATION LIST

Patent Literature

PTL 1: JP2006-151909A

SUMMARY OF INVENTION

Technical Problem

If hypertrophy of adipocytes can be suppressed by suppressing or preventing the accumulation of fat in adipocytes, body weight gain can be depressed. Further, the number of small adipocytes, which are normal mature adipocytes, can be maintained or increased, and physical conditions can be improved so that fat metabolism is easily promoted. The improved physical conditions facilitate the effect of improving fat metabolism by exercise, and prevent weight rebound caused by temporary overeating. Moreover, because adipocytes are less likely to be hypertrophied, the beauty effect of maintaining a slim body can be expected. In addition, the effect of preventing the generation of cellulite can also be expected.

Accordingly, an object of the present invention is to provide an obesity-suppressing composition (anti-obesity composition), particularly an obesity-suppressing composition that has the effect of suppressing fat accumulation in adipocytes. In particular, an object of the present invention is to provide an oral obesity-suppressing composition.

Solution to Problem

As a result of extensive studies concerning the above circumstances, the present inventors found that an excellent fat accumulation-suppressing effect could be achieved by ingesting a combination of at least one member selected from the group consisting of oleuropein and hydroxytyrosol, and at least one member selected from the group consisting of willow extract and sulforaphane. After further studies, the present invention has been completed.

More specifically, the present invention includes, for example, the main subjects described in the following items.

Item 1. An obesity-suppressing composition comprising the following components (A) and (B):
(A) at least one member selected from the group consisting of oleuropein and hydroxytyrosol;
(B) at least one member selected from the group consisting of sulforaphane compounds and willow extract.

Item 2. The obesity-suppressing composition according to item 1, wherein the composition comprises at least oleuropein.

Item 3. The obesity-suppressing composition according to item 1 or 2, wherein the composition comprises at least sulforaphane.

Item 4. The obesity-suppressing composition according to any one of items 1 to 3, wherein the composition comprises olive extract and component (B).

Item 5. The obesity-suppressing composition according to any one of items 1 to 4, wherein the composition is an oral composition.

Item a. A method for suppressing obesity, comprising orally administering the following components (A) and (B):
(A) at least one member selected from the group consisting of oleuropein and hydroxytyrosol;
(B) at least one member selected from the group consisting of sulforaphane compounds and willow extract.

Item b. The method for suppressing obesity according to item 1, wherein the method comprises orally administering at least oleuropein.

Item c. The method for suppressing obesity according to item 1 or 2, wherein the method comprises orally administering at least sulforaphane.

Item d. The method for suppressing obesity according to any one of items 1 to 3, wherein the method comprises orally administering olive extract and component (B).

Advantageous Effects of Invention

According to the present invention, fat accumulation in adipocytes can be suppressed, as described above. Therefore, the increase of hypertrophic adipocytes can be suppressed, and obesity can be prevented. Moreover, when the increase of hypertrophic adipocytes is suppressed, the abundance ratio of small adipocytes in adipocytes consequently increases, and thus, the efficiency of lipolysis relatively increases. Accordingly, the obesity-suppressing composition of the present invention not only prevents obesity, but also promotes weight loss, and makes it easier to achieve and maintain an ideal body shape.

DESCRIPTION OF EMBODIMENTS

The sulforaphane compound used in the present invention refers to sulforaphane and sulforaphane glucosinolate. Sulforaphane glucosinolate is a glycoside of sulforaphane. These sulforaphane compounds are known to be contained in large amounts in cruciferous plants, such as broccoli and cabbage. It is known that, for example, when such a plant is cut (e.g., cut with a knife or chewed), sulforaphane glucosinolate is hydrolyzed by myrosinase, which is an enzyme present in plants, to produce sulforaphane. A similar hydrolysis is known to also occur by the action of intestinal bacteria and digestive enzymes. Therefore, preferred examples of the sulforaphane compound in the present invention include crushed products (e.g., purees) and juices of cruciferous plants, and their dried products, fractionated products, purified products, etc. The proportion of the sulforaphane compound in the obesity-suppressing composition of the present invention is not particularly limited. For example, the proportion in terms of sulforaphane is preferably about 0.000001 to 0.5 mass %, and more preferably about 0.000005 to 0.25 mass %. The lower limit is more preferably 0.0001 mass % or more, and even more preferably 0.0005 mass % or more.

Further, the amount of the sulforaphane compound in the obesity-suppressing composition of the present invention is not particularly limited, but can be suitably selected according to the embodiment so that the amount in terms of sulforaphane is preferably 0.1 to 1.0 mg, more preferably 0.1 to 0.6 mg, and even more preferably 0.1 to 0.5 mg.

When the obesity-suppressing composition of the present invention is ingested, the amount of the sulforaphane compound ingested by an adult per day is not particularly limited, but can be suitably selected according to the embodiment so that the amount in terms of sulforaphane is preferably 0.1 to 1.0 mg, more preferably 0.1 to 0.6 mg, and even more preferably 0.1 to 0.5 mg.

The willow extract used in the present invention is extracted from a plant in the genus *Salix* or *Populus* of the family Salicaceae. Examples of plants in the genus *Populus* of the family Salicaceae include "Urajirohako yanagi" (synonyms: "Hakuyo" and "Gindoro"; *P. alba*), Canadian poplar (*P.* x *Canadensis*), cottonwood (*P. deltoides*) (synonym: "Hiroha hakoyanagi"), "Kotokake yanagi" (*P. euphratica*), "Oobayamanarashi" (*P. tomentosa*), "Chirimendoro" (*P. koreana*), "Doronoki" (*P. maximowiczii*), "Yoroppa kuroyamanarashi" (*P. nigra*), "Seiyo hakoyanagi" (synonym: "Italia yamanarashi"; *P. nigra* var. italica), "Yamanarashi" (synonyms: "Hakoyanagi" and "Popura"; *P. sieboldii*), balsam poplar (*P. tacamahaca*), "Shina yamanarashi," "Chosen yamanarashi" (*P. davidiana*), American poplar (*P. tremuloides*), and *P. euramericana*. Examples of plants in the genus *Salix* of the family Salicaceae include white willow (*S. alba*), "Saikoku kitsune yanagi" (*S. alopochroa*), "Yusuraba yanagi" (*S. aurita*), "Shidare yanagi" (synonym: "Ito yanagi"; *S. babylonica*), "Yamaneko yanagi" (synonym: "Bakko yanagi"; *S. bakko*), "Akame yanagi" (synonym: "Maruba yanagi"; *S. chaenomeloides*), "Koganeshidare" (*S. chrysochoma*), *S. daphnoides* (violet willow), "Salikkusu elaeagunosu" (*S. elaeagnos* 'Scopoli'), "Pokkiri yanagi" (*S. fragilis*), "Ookitsune yanagi" (synonym: "Kinme yanagi"; *S. futura*), "Kawayanagi" (synonym: "Nagaba kawa yanagi"; *S. gilgiana*), "Neko yanagi" (*S. gracilistyla*), "Kuro yanagi" (*S. gracilistyla* var. *melanostachys*), "Sause" (*S. humboldtiana*), "Inukori yanagi" (*S. integra*), "Shiba yanagi" (*S. japonica*), "Shiro yanagi" (*S. jessoensis*), "Kivu yanagi" (*S. kinuyanagi*), "Kori yanagi" (*S. koriyanagi*), "Ezo yanagi" (*S. rorida*), "Furisode yanagi" (*S. leucopithecia*), "Unryu yanagi" (*S. matsudana f. tortuosa*), "Takaneiwa yanagi" (synonym: "Rengeiwa yanagi"), "Ooshidare yanagi" (*S. ohsidare*), "Ezomame yanagi" (*S. nummularia* ssp. *Pauciflora*), "Ezonokinu yanagi" (*S. pet-susu*), *S. purpurea* (purple willow), "Kouhiryu," "Miyama yanagi" (synonym: "Mineyanagi"; *S. reinii*), "Komaiwa yanagi" (*S. rupifraga*), "Onoe yanagi" (synonym: "Karafuto yanagi"; *S. sachalinensis*), "Kogome yanagi" (*S. serissaefolia*), "Shirai yanagi" (*S. shiraii*), *Salix* sp, "Tachi yanagi" (*S. subfragilis*), "Noyanagi" (synonym: "Himeyanagi"), "Seiyotachi yanagi," "Kitsune yanagi" (synonym: "Iwayanagi"; *S. vulpine*), and "Ezonotakane yanagi" (*S. yezoalpina*). Preferred among these are plants in the genus *Salix* of the family Salicaceae; and more preferred are *Salix daphnoides* (violet willow), *Salix purpurea* (purple willow), *Salix fragilis* (Pokkiri yanagi), and *Salix alba* (white willow). These can be used singly or in a combination of two or more in the extraction. As the extraction site, buds (including young branches), leaves, branches, trunk, and bark of willow can be used singly or in any combination thereof. Preferred among these are buds (including young branches) and bark. In the extraction, these extraction sites of willow can be preferably used after cutting, crushing, and grinding. Further, the extract can be preferably subjected to drying and other treatments. Examples of the willow extract include "Salicis cort extract (produced by Frutarom Switzerland Ltd.)," which complies with the standards of the European Pharmacopoeia and the German Pharmacopoeia. Specifically, a widely available extract is "Salicis cort extract (produced by Frutarom Switzerland Ltd.)," which is an extract powder obtained by extracting bark and/or sprouts and young branches of one or more plants selected from the group consisting of *Salix purpurea*, *Salix daphnoides*, and *Salix fragilis*, using water.

Willow is extracted using a solvent by still standing, shaking, or stirring under conditions such as ultrasonic irradiation, heating, or pressure still standing. These extraction methods and conditions can be freely combined, as required. As the extraction solvent to be used, an aqueous solvent and an organic solvent can be used as extractants, and they can be used singly or in combination. Moreover, when supercritical fluid extraction is used, a supercritical fluid obtained by rendering a compound that is liquid or gas at ordinary temperature in a supercritical state is used. Examples of organic solvents include lower alcohols, such as ethyl alcohol, propanol, isopropanol, and butanol; polyhydric alcohols, such as polyethylene glycol, propylene glycol, 1,3-butylene glycol, and dipropylene glycol; ethyl acetate, butyl acetate, and like esters; ketones, such as acetone and methyl ethyl ketone; and supercritical fluids, such as carbon dioxide, methyl alcohol, and ammonia. In some embodiments, preferred examples of the extraction solvent include water, ethyl alcohol, and a mixture thereof. In some embodiments, water is used as the extraction solvent. The temperature of the extraction solvent during extraction (extraction temperature) is preferably 3° C. to the boiling point of the extraction solvent used, except for extraction using a supercritical fluid solvent or extraction under pressurized conditions. In general, extraction is preferably performed by heating at a temperature higher than room temperature. The hot water or boiling extraction time is suitably determined depending on, for example, the type of extraction solvent and the extraction temperature. The extract obtained by extraction as described above can be further subjected to various treatments, as necessary. Examples of treatments include fraction, purification, concentration, drying, and the like. In the case of a powder or other solid form, dextrin, crystalline cellulose, corn starch, or like excipient can be added.

The oleuropein used in the present invention is a polyphenolic substance, and is contained in a large amount in flowers, peel, fruit, leaves, bark, roots, or seeds, particularly leaves and fruit, of plants in the genus Olea of the family Oleaceae. Products obtained by extracting these plants and further purifying the resulting extract to increase the oleuropein content can be preferably used. Examples of plants in the genus Olea of the family Oleaceae that can be used in the extraction include olives (*Olea europaea* Linne) and congeners thereof (e.g., *Olea welwitschii* and *Olea paniculata*). Typical examples of these varieties include Nevadillo blanco, Manzanillo, Picual, Hojiblanca, Arbequina, Kalamata, Koroneiki, Picholine, Paragon, Wagga Verdale, Mission, Washington, West Australia Mission, South Australia Vendor, Azapa, Barnea, Cornicabra, Gordal, Frantoio, Leccino, Cipressino, Lucca, Ascolana tenera, Correggiola, Moraiolo, Black Italian, Coratina, Helena, Rosciola, One seven seven, El Greco, and Hardy's Mammoth. Synthesized oleuropein can also be used.

Olive extract obtained by extracting olive leaves, olive fruit, etc., with a solvent, and optionally performing separation, purification, and other treatments, contains oleuropein, and can be preferably used in the present invention. The olive extract preferably has an oleuropein content of 15 mass % or more, more preferably 20 mass % or more, and even more preferably 30 mass % or more. On the other hand, when unrefined olive extract is used in the present invention, the oleuropein content may be low in some cases, and many components other than oleuropein may also be contained. Therefore, when unrefined olive extract is used, it is preferably used within the range in which the effects of the present invention are exhibited, with care exercised for the oleuropein content. Therefore, refined olive extract is preferably used.

Examples of the solvent used for extraction include water and ethanol, as well as light petroleum, hexane, butanol, propanol, methanol, polyethylene glycol, propylene glycol, butylene glycol, and a mixture of these solvents. Preferred among these is water or a mixture of water and ethanol (water-ethanol mixture). The mixing ratio of water to ethanol in the water-ethanol mixture is, by volume ratio, preferably about 100:1 to 1:200, more preferably about 20:1 to 1:20, and most preferably about 1:9 to 1:1.

Regarding the extraction method, the solvent temperature, the weight ratio of the solvent to the raw materials, or the extraction time can be freely determined for each of the various raw materials and the solvent used. The temperature of the solvent during extraction may be within the range of about −4° C. to about 200° C., and is preferably about 30° C. to about 150° C., and more preferably about 40° C. to about 80° C.

When olive leaves are used for extraction, it is preferable to use olive green leaves with a high oleuropein content. In particular, it is also preferable to use dried leaves obtained by drying green leaves. The drying method is not limited. For example, it is preferable to use olive leaves with a high oleuropein content obtained by the method disclosed in JP2003-335693A, etc.

Similarly, when olive fruit is used, oleuropein is generated in immature olive fruit, and starts to be accumulated therein; and then, when the fruit is matured to the degree that its appearance is greenish yellow, the effect of increasing the amount of oleuropein accumulated tends to disappear. Accordingly, it is preferable to use mature fruit. Particularly preferred mature fruit has an appearance of green to greenish yellow color.

Preferred examples of the olive extract used in the present invention include olive leaf extract or olive fruit extract obtained by subjecting a solvent crude extracted solution of olive leaves or olive fruit to distillation, filtration, or like treatment to remove the solvent, then passing the resultant through a resin column filled with, for example, a styrene-divinylbenzene polymer resin (Diaion HP20, produced by Mitsubishi Chemical), Amberlite XAD resin (produced by Rohm and Haas), or Duolite S resin (produced by Diamond Shamrock), to adsorb oleuropein, performing desorption, and concentrating the resulting solution under reduced pressure, followed by drying. As a result of these treatments, not only can the oleuropein content be increased 3 to 6 times higher than that of the crude extract, but also the mixing rate of other components can be significantly reduced.

Such raw materials having an increased oleuropein content are also commercially available. Examples thereof include olive leaf dry extract (produced by Frutarom; oleuropein content: 18 to 26%), an olive leaf extract powder (produced by Biofronte; oleuropein content: about 40%), olive leaf extract (produced by Bio Actives Japan; oleuropein content: about 25%), Opiace (produced by Eisai Food & Chemical Co., Ltd.; oleuropein content: about 35%), and the like.

The proportion of oleuropein in the obesity-suppressing composition of the present invention is not particularly limited. For example, it is preferably about 0.0005 to 30 mass %, and more preferably about 0.001 to 25 mass %. The lower limit is more preferably 0.005 mass % or more, and even more preferably 0.01 mass % or more.

Further, the amount of oleuropein in the obesity-suppressing composition of the present invention is not particularly limited, and can be suitably selected according to the embodiment so that it is preferably 30 to 130 mg, more preferably 30 to 110 mg, and even more preferably 30 to 70 mg.

When the obesity-suppressing composition of the present invention is ingested, the amount of oleuropein ingested by an adult per day is not particularly limited, but can be suitably selected according to the embodiment so that it is preferably 30 to 130 mg, more preferably 30 to 110 mg, and even more preferably 30 to 70 mg.

The hydroxytyrosol used in the present invention is one of the structure skeletons of oleuropein, and can be efficiently obtained by hydrolyzing oleuropein. Since a large amount of oleuropein is contained in flowers, peel, fruit, leaves, bark, roots, or seeds, particularly leaves and fruit, of plants in the genus *Olea* of the family Oleaceae, hydroxytyrosol is generally obtained by hydrolyzing crude extract obtained by extracting plants in the genus *Olea*, or extract treated to increase the oleuropein content, as described above, and optionally further performing separation, purification, and other treatments. Olive extract before hydrolysis also contains hydroxytyrosol. Olive extract containing a larger amount of hydroxytyrosol can be prepared by performing hydrolysis. Examples of plants in the genus *Olea* of the family Oleaceae that can be used in the above extraction include olive (*Olea europaea* Linne) and congeners thereof (e.g., *Olea welwitschii* and *Olea paniculata*). Typical examples of these varieties are the same as described above, and include Nevadillo Blanco, Manzanillo, Picual, Hojiblanca, Arbequina, Kalamata, Koroneiki, Picholine, Paragon, Wagga Verdale, Mission, Washington, West Australia Mission, South Australia Vendor, Azapa, Barnea, Cornicabra, Gordal, Frantoio, Leccino, Cipressino, Lucca, Ascolana tenera, Correggiola, Moraiolo, Black Italian, Coratina, Helena, Rosciola, One seven seven, El Greco, and Hardy's Mammoth. Synthesized hydroxytyrosol can also be used.

Olive extract obtained by extracting olive leaves, olive fruit, etc., with a solvent, and optionally performing separation, purification, and other treatments, contains hydroxytyrosol in addition to oleuropein, and can be preferably used in the present invention. Furthermore, an olive extract processed product obtained by hydrolyzing the olive extract by a known method, and optionally further performing separation, purification, and other treatments, contains a large amount of hydroxytyrosol, and can also be preferably used in the present invention. The olive extract or olive extract processed product preferably has a hydroxytyrosol content of 5 mass % or more, more preferably 10 mass % or more, and even more preferably 20 mass % or more.

Olive extract containing hydroxytyrosol can be prepared in the same manner as in the preparation of olive extract containing oleuropein described above. For example, the solvent used in the extraction, and the extraction method can be the same as those described above.

Moreover, the following olive extract processed products (hydrolyzed products) can also be preferably used in the present invention: an olive extract processed product obtained by subjecting a solvent crude extracted solution of olive leaves or olive fruit to distillation, filtration, or like treatment to remove the solvent, and performing hydrolysis by a known method, such as an acidic hydrolysis method, optionally followed by concentration; an olive extract processed product obtained by passing the hydrolyzed product through a resin column to adsorb hydroxytyrosol, and then performing desorption; and an olive extract processed product obtained by concentrating the extract obtained by desorption under reduced pressure, followed by drying, and optionally mixing the resultant with an excipient. The hydroxytyrosol content of the extract can be adjusted by these treatments (particularly hydrolysis).

Such raw materials containing hydroxytyrosol are also commercially available. Examples thereof include OliveX HT6 (produced by GRAP'SUD; hydroxytyrosol content: about 6%), OliveX CEO10 (produced by GRAP'SUD; hydroxytyrosol content: about 10%), olive leaf extract (produced by Bio Actives Japan; hydroxytyrosol content: about 7%), Oralis (produced by Eisai Food & Chemical Co., Ltd.; hydroxytyrosol content: about 20%), and the like. As described above, the olive leaf extract powder (produced by Biofronte) also contains about 40% oleuropein.

The proportion of hydroxytyrosol in the obesity-suppressing composition of the present invention is not particularly limited. For example, the proportion of hydroxytyrosol is preferably about 0.0001 to 25 mass %, and more preferably about 0.0005 to 20 mass %. The lower limit is more preferably 0.01 mass % or more, and even more preferably 0.05 mass % or more.

Further, the amount of hydroxytyrosol in the obesity-suppressing composition of the present invention is not particularly limited, but can be suitably selected according to the embodiment so that it is preferably 10 to 110 mg, more preferably 20 to 90 mg, and even more preferably 30 to 70 mg, When the obesity-suppressing composition of the present invention is ingested, the amount of hydroxytyrosol ingested by an adult per day is not particularly limited, but can be suitably selected according to the embodiment so that it is preferably 10 to 110 mg, more preferably 20 to 90 mg, and even more preferably 30 to 70 mg.

The obesity-suppressing composition of the present invention can be used as an oral composition, such as a food and drink composition, an oral pharmaceutical composition, or an oral quasi-drug composition. Examples of food and drink compositions include foods eaten for the purpose of weight loss, diet, or dietary therapy of diabetes, etc., foods for specified health use, dietary supplements, functional foods, foods for elderly people, and the like.

The form of the obesity-suppressing composition of the present invention is not particularly limited. When the obesity-suppressing composition is an oral composition, examples of its form include liquids, tablets, chewable tablets, foaming tablets, troches, drops, (hard or soft) capsules, granules, powders, drink powders (prepared before use by dissolving the powder in a solvent, such as water, for drinking), pills, dry syrups, infusions, decoctions, confections, chewing gum, syrups, beverages, spirits, oral disintegrators, gels/jellies, whips, sprays, pastes, sheets, pastes, gels (e.g., jellies), and the like. When the oral composition is formed into a liquid, the best form is, for example, a two-agent type drink in which liquid and solid are separated, and mixed before drinking, in order to increase the stability of the active ingredient.

The foods and drinks of the present invention are generally supplied as bottled foods and drinks. The bottled foods and drinks in the present invention refer to foods and drinks supplied for consumers in a state in which the obesity-suppressing composition of the present invention in the form of foods and drinks is filled and sealed in containers. The containers mentioned herein refer to glass bottles, synthetic resin bottles, sheet materials made of composites of synthetic resin, laminate materials, etc. (e.g., bags, easy-peel assemblies, and pouches), paper containers, metal cans, PTP packages, and the like.

In particular, when the obesity-suppressing composition of the present invention is an oral composition, the composition may contain known components generally used in foods, pharmaceuticals, etc., other than oleuropein, hydroxytyrosol, willow extract, and sulforaphane, within a range that does not impair the effects of the present invention. For example, the composition may contain other components (including foods as well as food additives) generally added to foods, including conventionally known food additives, such as excipients, binders, emulsifiers, sweeteners, acidulants, fortifiers, dietary fiber, antioxidants, seasonings, fragrances, coloring agents, lubricants, and polysaccharide thickeners. Such known components can be used singly or in a combination of two or more.

Examples of excipients include sugar alcohols, such as maltitol, xylitol, sorbitol, and erythritol; crystalline cellulose, lactose, sucrose, glucose, dextrin, starch, carbonates, phosphates, and the like.

Examples of binders include gelatin, alginic acid, xanthan gum, cellulose, hydroxypropyl cellulose, methyl cellulose, carrageenan, pullulan, pectin, and the like.

Examples of emulsifiers include sucrose fatty acid ester, maltose fatty acid ester, lactose fatty acid ester, and like sugar fatty acid esters; sorbitan fatty acid ester, fatty acid monoglyceride, polyoxyethylene sorbitan fatty acid ester, polyoxyethylene glycerol fatty acid ester, polyoxyethylene sorbit fatty acid ester, polyethylene sterol, alkyl glucoside, phospholipid, and like surfactants; and starch solutions, gelatin solutions, hydroxypropyl cellulose, hydroxypropyl methylcellulose, hydroxyethyl cellulose, crystalline cellulose, powdered cellulose, carboxymethyl cellulose, methyl cellulose, ethyl cellulose, gum arabic powder, pullulan, pectin, dextrin, corn starch, pregelatinized starch, gelatin, xanthan gum, gellan gum, carrageenan, tragacanth, tragacanth powder, macrogol, and like polymers. These can be used singly or in a combination of two or more.

Examples of sweeteners include saccharin, sodium saccharin, acesulfame potassium, stevia extract, stevioside, sucralose, neohesperidyl dihydrochalcone, glycyrrhizin, perillatin, thaumatin, aspartylphenylalanine methyl ester, methoxycinnamic aldehyde, trehalose, erythritol, sorbitol, palatinose, Palatinit, xylitol, maltose, lactitol, fructose, reduced palatinose, glucose, sugar, soft brown sugar, refined honey, unrefined honey, reduced starch syrup, starch syrup, isomerized sugar (high-fructose corn syrup, etc.), and the like. These sweeteners can be used singly or in a combination of two or more.

Examples of acidulants include fruit acids, such as citric acid, gluconic acid, malic acid, and tartaric acid; acetic acid, lactic acid, phosphoric acid, succinic acid, glutamic acid, and the like.

Examples of fortifiers include vitamins, minerals, amino acids, animal and plant extract, peptides, and the like.

Dietary fiber can be water-soluble or water-insoluble. Examples thereof include indigestible dextrin, cellulose (pulp), apple fiber, potato dextrose, psyllium, beet fiber, gum arabic, and the like.

Examples of antioxidants include dibutylhydroxytoluene, ascorbic acid, erythorbic acid, tocopherol, tea extract such as catechin and green tea polyphenol; rutins, such as rutin (extract), quercetin, rutin enzyme-decomposed product, enzyme-treated rutin (extract), and enzyme-treated isoquercitrin; enzyme-decomposed apple extract; emulsifiers, such as sucrose fatty acid ester, sorbitan fatty acid ester, enzyme-treated lecithin, enzyme-decomposed lecithin, and saponin; and the like.

The obesity-suppressing composition of the present invention, particularly when orally taken, can improve physical conditions so that fat is easily decomposed, and can enhance the diet effect obtained by diet control or exercise. Further, the effect of improving fat decomposition capacity under normal conditions can be obtained. Accordingly, the present invention can be optimally used as, for example, diet foods, weight-reducing foods, foods for exercise therapy, obesity-treatment foods, and foods and drinks for persons with extremely low physical activity because of disease, motor dysfunction, advanced age, etc. The present invention can also be used as foods and drinks labeled with an indication that they are suitable for diet, beauty care, or obesity improvement. Moreover, due to the effect of preventing the generation of hypertrophic adipocytes, the present invention can contribute to the prevention and improvement of obesity, diabetes, and various related diseases, and can also be used as oral compositions, pharmaceuticals, foods and drinks, etc., for preventing and improving obesity, metabolic syndrome, diabetes, arteriosclerosis, abnormal glucose tolerance, hypertension, hyperlipidemia, hyper neutral lipemia, hypercholesterolemia, hepatic disease, and the like. Furthermore, the present invention can also be used as oral compositions, pharmaceuticals, foods and drinks, etc., for preventing and improving complications of obesity and diabetes, such as periodontal'diseases (gingivitis and periodontitis), and can also be used as oral compositions (including foods and drinks) labeled with an indication that they are suitable for preventing or improving the above diseases.

EXAMPLES

The present invention is described in detail below; however, the present invention is not limited to the following examples. Hereinafter, "%" indicates "mass %," unless otherwise stated.

Suppression of Fat Droplet Accumulation in Adipocytes

The effect of suppressing fat droplet accumulation in adipocytes was evaluated using preadipocyte 3T3-L1 cells. The 3T3-L1 cells are isolated from mouse fibroblasts as cells accumulating fat. Because they are immortalized cells, they can be mass-produced as fibroblasts before induction of differentiation. Moreover, 95% or more of 3T3-L1 cells can differentiate into adipocytes by insulin, dexamethasone, and 3-isobutyl-1-methylxanthine (IBMX).

Preparation of Media

The passage media used were passage medium A (DMEM (4.5 g/L Glu), (Sigma, glucose, D5769), 10% BS (Gibco, 16170), and 1% antibiotic (Gibco, Antibiotic-Antimycotic, 15240-062)) and passage medium B (DMEM (4.5 g/L Glu), 10% FBS (Biowest, S1560), and 1% antibiotic).

The differentiation-inducing medium used was prepared by adding a 10-μg/mL insulin solution (Wako, 093-06351), 0.25 μM Dexamethasone (Sigma, D4902), and 0.11-mg/mL 3-isobutyl-1-methylxanthine (Sigma, 15879) to passage medium B. The differentiation-promoting medium used was prepared by adding a 5-μg/mL insulin solution to passage medium B. The differentiation-inducing medium and the differentiation-promoting medium were prepared before use.

Method for Preparing Samples

The oleuropein used was an "oleuropein" reagent available from Sigma. In the experiment, the oleuropein was used in such an amount that the final concentration was 50 μM.

The hydroxytyrosol used was a "hydroxytyrosol" reagent available from Sigma. In the experiment, the hydroxytyrosol was used in such an amount that the final concentration was 25 μM.

The willow extract used was a water extract (dry powder) of young branches including sprouts of willow (a plant mixture containing at least one or more members selected from *Salix daphnoides, Salix purpurea, Salix fragilis,* and *Salix alba*). In the experiment, the extract was diluted with the medium so that the final concentrations were 2.5, 5, 12.5, 25, 50, 100, and 200 μg/mL.

The sulforaphane used was a "sulforaphane" reagent available from Sigma. In the experiment, a 100-mM DMSO solution was prepared, and diluted with the medium.

A 5-mM γ-orizanol solution was prepared, and diluted with the medium.

Method for Culturing Cells and Adding Samples

A necessary amount of 3T3-L1 cells (produced by Sumitomo Dainippon Pharma Co., Ltd.; Embryo mouse) was grown in passage medium A. The cell suspension (1 mL) was seeded in a collagen-coated culture plate (produced by Sumitomo Bakelite Co., Ltd.; Sumilon Celltight C-1) so that the concentration was $2.5 \times 10^4$ cells/well. The cells were cultured for 2 days at 37° C. in the presence of 5% $CO_2$.

Thereafter, the medium was replaced with passage medium B. After confluent growth, culture was continued for about 2 days in passage medium B, and the medium was replaced with the differentiation-inducing medium (Day 0). Within 48 hours after the differentiation of the cells was induced in the differentiation-inducing medium, the medium was replaced with the differentiation-promoting medium (Day 2). Each sample was continuously added from the time of the replacement of the differentiation-inducing medium (Day 0) to Day 7 or 8. The samples were added according to the compositions shown in Tables 1 to 4.

Method for Staining Adipocytes with Oil Red

Preparation of Reagent

Cold 10% formalin/PBS was prepared by adding 10% (v/v) formalin to PBS (phosphate buffered saline) and adjusting the pH to 7.4, and then stored at 4° C. In this experiment, a 10% neutral buffered formalin solution (Wako, 060-03845) was used.

The stain solution used was a 0.5% Oil Red O/isopropanol solution. Oil Red O (Wako, 154-02072) was dissolved in isopropanol (Sigma) by shaking to prepare a saturated solution. The 0.5% Oil Red 0/isopropanol solution and distilled water were mixed at a ratio of 3:2 immediately before use (preparation before use).

Staining Method

The 3T3-L1 cells in the well plate cultured to Day 7 or 8 by the above culture method were used. Cold 10% formalin/PBS (0.5 mL/well) was added to the well plate containing the medium, and allowed to stand at room temperature. After the medium was removed, cold 10% formalin/PBS (0.5 mL/well) was newly added, and allowed to stand at room temperature. After the formalin solution was removed, the well plate was washed 2 or 3 times with distilled water (1 mL/well) to completely remove the remaining distilled water. After the well plate was washed once with 60% isopropanol (0.5 mL/well), the filtered stain solution was added at 1 mL/well, and allowed to stand at room temperature. After staining, the well plate was washed once with 60% isopropanol (0.5 mL/well), and washed 2 or 3 times with distilled water (1 mL/well). The resultant was dissolved in 100% isopropanol (0.5 mL/well), the plate side was wrapped with parafilm, and extraction was performed while gently shaking at 20° C. for 20 minutes. The eluted isopropanol solution was measured by a microplate reader at OD 490 nm. The measurement results were shown as values relative to the amount of fat accumulation in adipocytes in a medium to which nothing was added, which was regarded as 100. Tables 1 to 4 show the results.

TABLE 1

|  | Unit | Example | | | |
|---|---|---|---|---|---|
|  |  | 1a | 2a | 3a | 4a |
| Oleuropein | µM | 50 | 50 | 50 | 50 |
| Willow extract | µg/mL | 25 | — | — | — |
| Sulforaphane | µM | — | 0.5 | 1.0 | 1.25 |
| Relative amount of fat accumulation |  | 47.8 | 79.6 | 79.2 | 74.0 |

TABLE 2

|  | Unit | Comparative Example | | | | | | | |
|---|---|---|---|---|---|---|---|---|---|
|  |  | 1a | 2a | 3a | 4a | 5a | 6a | 7a | 8a |
| Oleuropein | µM | 50 | — | — | — | — | — | 50 | — |
| Willow extract | µg/mL | — | 25 | — | — | — | — | — | — |
| Sulforaphane | µM | — | — | 0.5 | 1.0 | 1.25 | — | — | — |
| γ-Orizanol | µM | — | — | — | — | — | 2.5 | 2.5 | — |
| Relative amount of fat accumulation |  | 99.9 | 61.9 | 110.7 | 109.8 | 100.9 | 51.4 | 64.5 | 100.0 |

TABLE 3

|  | Unit | Example | | | |
|---|---|---|---|---|---|
|  |  | 1b | 2b | 3b | 4b |
| Hydroxytyrosol | µM | 37.5 | 12.5 | 25 | 37.5 |
| Willow extract | µg/mL | 12.5 | — | — | — |
| Sulforaphane | µM | — | 0.25 | 1.25 | 2.5 |
| Relative amount of fat accumulation |  | 50.0 | 84.7 | 72.3 | 58.7 |

TABLE 4

|  | Unit | Comparative Example | | | | | | | |
|---|---|---|---|---|---|---|---|---|---|
|  |  | 1b | 2b | 3b | 4b | 5b | 6b | 7b | 8b |
| Hydroxytyrosol | µM | — | 25 | 37.5 | — | — | — | — | 37.5 |
| Willow extract | µg/mL | — | — | — | 12.5 | — | — | — | — |
| Sulforaphane | µM | — | — | — | — | 0.25 | 2.5 | — | — |
| γ-Orizanol | µM | — | — | — | — | — | — | 0.5 | 0.5 |
| Relative amount of fat accumulation | | 100.0 | 99.3 | 78.4 | 75.9 | 104.8 | 100.8 | 78.5 | 76.7 |

As shown in Tables 1 and 2, when the amount of fat accumulation in adipocytes in a medium to which nothing was added was regarded as 100 (Comparative Example 8a), the relative amount of fat accumulation in adipocytes cultured in media to which 50 µM of oleuropein and 0.5 to 1.25 µM of sulforaphane were each added was around 100. These results were almost the same as the amount of fat accumulation in the control. When willow extract was added (61.9; Comparative Example 4a), or when γ-orizanol was added (51.4; Comparative Example 6a), the amount of fat accumulation in each case was less than that of the control (Comparative Example 8a). In contrast, when oleuropein and sulforaphane were added in combination, the amount of fat accumulation was 79.6 to 74.0 at a sulforaphane concentration of 0.5 to 1.25 µM. Thus, the effect of suppressing fat accumulation was confirmed. It was also found that the effect of suppressing fat accumulation could be enhanced by using willow extract in combination with oleuropein, which alone had no effect. On the other hand, the combined use of oleuropein with γ-orizanol, which had a high fat accumulation-suppressing effect, did not enhance the fat accumulation-suppressing effect. These results demonstrate that fat accumulation in adipocytes could be significantly suppressed by using willow extract or sulforaphane in combination with oleuropein.

Furthermore, as shown in Tables 3 and 4, when the amount of fat accumulation in adipocytes in a medium to which nothing was added was regarded as 100 (Comparative Example 1b), the relative amount of fat accumulation in adipocytes cultured in media to which each component was added was as follows. When 25 µM of hydroxytyrosol, or 0.25 or 2.5 µM of sulforaphane was added, the amount of fat accumulation was around 100 in all cases. These results were almost the same as the amount of fat accumulation in the control (Comparative Example 1b). When 37.5 µM of hydroxytyrosol, 12.5 µg/mL of willow extract, or 0.5 µM of γ-orizanol was added, the amount of fat accumulation was 75 to 80 in all cases; their accumulation-suppressing effects were about 25% higher than that of the control. In contrast, when hydroxytyrosol and sulforaphane were added in combination, their suppressing effects were 20 to 30% higher, even when they were combined at a concentration in which hydroxytyrosol and sulforaphane alone exhibited no effect of suppressing fat accumulation. Moreover, when 37.5 µM of hydroxytyrosol, 12.5 µg/mL of willow extract, or 0.5 µM of γ-orizanol was added, their fat accumulation-suppressing effects were about 25% higher than that of the control. However, when these components were added in combination, the combination of hydroxytyrosol and willow extract showed about a 50% suppressing effect; whereas the combination of hydroxytyrosol and γ-orizanol showed 76.7, which was the same as the suppressing effect of the individual components. Thus, the combined use of hydroxytyrosol and γ-orizanol did not enhance the fat accumulation-suppressing effect. These results demonstrate that fat accumulation in adipocytes could be suppressed by using willow extract or sulforaphane in combination with hydroxytyrosol.

The formulation of the Examples of the obesity-suppressing compositions (particularly oral compositions) according to the present invention is described below; however, the present invention is not limited to the following formulation examples. The amounts indicated are mass %, unless otherwise stated.

Formulation Example 1: Sports Drink Powder

| Raw material | Amount |
| --- | --- |
| Olive leaf extract (containing 20% oleuropein) | 0.9 |
| Broccoli sprout extract (containing 2% sulforaphane) | 0.1 |
| Fruit juice powder | 17 |
| Sodium chloride | 7 |
| Citric acid | 4 |
| Trisodium citrate | 1.5 |
| Magnesium chloride | 0.03 |
| Potassium chloride | 0.06 |
| Fragrance | 1 |
| Fructose | Remainder |
| Total | 100 |

30 g per pack is dissolved in 500 mL of water for drinking. For each drink, the amount of oleuropein is 54 mg, and the amount of sulforaphane is 0.6 mg.

Formulation Example 2: Sports Drink Powder

| Raw material | Amount |
| --- | --- |
| Olive leaf extract (containing 35% oleuropein) | 0.4 |
| Broccoli sprout extract (containing 2% sulforaphane) | 0.07 |
| Fruit juice powder | 17 |
| Sodium chloride | 7 |
| Citric acid | 4 |
| Trisodium citrate | 1.5 |
| Magnesium chloride | 0.03 |
| Potassium chloride | 0.06 |
| Fragrance | 1 |
| Fructose | Remainder |
| Total | 100 |

30 g per pack is dissolved in 500 mL of water for drinking. For each drink, the amount of oleuropein is 42 mg, and the amount of sulforaphane is about 0.4 mg.

Formulation Example 3: Sports Drink Powder

| Raw material | Amount |
| --- | --- |
| Olive leaf extract (containing 40% oleuropein) | 0.9 |
| Broccoli sprout extract (containing 2% sulforaphane) | 0.3 |
| Fruit juice powder | 17 |
| Sodium chloride | 7 |
| Citric acid | 4 |
| Trisodium citrate | 1.5 |
| Magnesium chloride | 0.03 |
| Potassium chloride | 0.06 |
| Fragrance | 1 |
| Fructose | Remainder |
| Total | 100 |

30 g per pack is dissolved in 500 mL of water for drinking. For each drink, the amount of oleuropein is about 110 mg, and the amount of sulforaphane is 1.8 mg.

Formulation Example 4: Tea Powder

| Raw material | Amount |
| --- | --- |
| Olive leaf extract (containing 20% oleuropein) | 7.5 |
| Broccoli sprout extract (containing 2% sulforaphane) | 1.25 |
| Fragrance | 15 |
| Fructose | Remainder |
| Total | 100 |

2 g per pack is dissolved in 150 mL of water for drinking. For each drink, the amount of oleuropein is 30 mg, and the amount of sulforaphane is 0.5 mg.

Formulation Example 5: Tea Powder

| Raw material | Amount |
| --- | --- |
| Olive leaf extract (containing 35% oleuropein) | 7.5 |
| Broccoli sprout extract (containing 2% sulforaphane) | 2 |
| Fragrance | 15 |
| Fructose | Remainder |
| Total | 100 |

2 g per pack is dissolved in 150 mL of water for drinking. For each drink, the amount of oleuropein is 52.2 mg, and the amount of sulforaphane is 0.8 mg.

Formulation Example 6: Tea Powder

| Raw material | Amount |
| --- | --- |
| Olive leaf extract (containing 25% oleuropein) | 14 |
| Broccoli sprout extract (containing 2% sulforaphane) | 1.5 |
| Fragrance | 15 |
| Fructose | Remainder |
| Total | 100 |

2 g per pack is dissolved in 150 mL of water for drinking. For each drink, the amount of oleuropein is 70 mg, and the amount of sulforaphane is 0.6 mg.

Formulation Example 7: Baked Goods

| Raw material | Amount |
| --- | --- |
| Olive leaf extract (containing 20% oleuropein) | 1 |
| Broccoli sprout extract (containing 2% sulforaphane) | 0.1 |
| Reduced starch syrup | 20 |
| Rice oil | 15 |
| Baking powder | 1.5 |
| Salt | 1 |
| Fragrance | 0.3 |
| Water | 15 |
| Soft flour | Remainder |
| Total | 100 |

Subdivided packs each containing 5 baked goods (10 g/piece). For each pack, the amount of oleuropein is 100 mg, and the amount of sulforaphane is 1 mg.

Formulation Example 8: Baked Goods

| Raw material | Amount |
| --- | --- |
| Olive leaf extract (containing 20% oleuropein) | 1.3 |
| Broccoli sprout extract (containing 2% sulforaphane) | 0.1 |
| Reduced starch syrup | 20 |
| Rice oil | 15 |
| Baking powder | 1.5 |
| Salt | 1 |
| Fragrance | 0.3 |
| Water | 15 |
| Soft flour | Remainder |
| Total | 100 |

Subdivided packs each containing 5 baked goods (10 g/piece). For each pack, the amount of oleuropein is 130 mg, and the amount of sulforaphane is 1 mg.

Formulation Example 9: Baked Goods

| Raw material | Amount |
| --- | --- |
| Olive leaf extract (containing 35% oleuropein) | 0.57 |
| Broccoli sprout extract (containing 2% sulforaphane) | 0.1 |
| Reduced starch syrup | 20 |
| Rice oil | 15 |
| Baking powder | 1.5 |
| Salt | 1 |
| Fragrance | 0.3 |
| Water | 15 |
| Soft flour | Remainder |
| Total | 100 |

Subdivided packs each containing 5 baked goods (10 g/piece). For each pack, the amount of oleuropein is about 100 mg, and the amount of sulforaphane is 1 mg.

Formulation Example 10: Capsules

| Raw material | Amount |
| --- | --- |
| Olive leaf extract (containing 40% oleuropein) | 60 |
| Broccoli sprout extract (containing 2% sulforaphane) | 8 |

-continued

| Raw material | Amount |
| --- | --- |
| Sucrose fatty acid ester | 3 |
| Corn starch | Remainder |
| Total | 100 |

Functional food eaten by taking 3 gelatin hard capsules each containing 150 mg at a time. For each intake, the amount of oleuropein is about 110 mg, and the amount of sulforaphane is about 0.7 mg.

Formulation Example 11: Capsules

| Raw material | Amount |
| --- | --- |
| Olive leaf extract (containing 40% oleuropein) | 55 |
| Broccoli sprout extract (containing 2% sulforaphane) | 11 |
| Sucrose fatty acid ester | 3 |
| Corn starch | Remainder |
| Total | 100 |

Functional food eaten by taking 3 gelatin hard capsules each containing 150 mg at a time. For each intake, the amount of oleuropein is 99 mg, and the amount of sulforaphane is about 1 mg.

Formulation Example 12: Capsules

| Raw material | Amount |
| --- | --- |
| Olive leaf extract (containing 35% oleuropein) | 45 |
| Broccoli sprout extract (containing 2% sulforaphane) | 10 |
| White willow extract | 5 |
| Sucrose fatty acid ester | 3 |
| Corn starch | Remainder |
| Total | 100 |

Functional food eaten by taking 3 gelatin hard capsules each containing 150 mg at a time. For each intake, the amount of oleuropein is about 70 mg, and the amount of sulforaphane is about 0.9 mg.

Formulation Example 13: Tablets

| Raw material | Amount |
| --- | --- |
| Olive leaf extract (containing 40% oleuropein) | 45 |
| Broccoli sprout extract (containing 2% sulforaphane) | 10 |
| Cellulose | 10 |
| Sucrose fatty acid ester | 3 |
| Reduced maltose starch syrup | Remainder |
| Total | 100 |

Functional food eaten by taking 2 tablets obtained by tableting 200 mg of the above composition at a time. For each intake, the amount of oleuropein is about 70 mg, and the amount of sulforaphane is 0.8 mg.

Formulation Example 14: Tablets

| Raw material | Amount |
| --- | --- |
| Olive leaf extract (containing 35% oleuropein) | 50 |
| White willow extract | 5 |
| Cellulose | 10 |
| Sucrose fatty acid ester | 3 |
| Reduced maltose starch syrup | Remainder |
| Total | 100 |

Functional food eaten by taking 2 tablets obtained by tableting 200 mg of the above composition at a time. For each intake, the amount of oleuropein is about 70 mg.

Formulation Example 15: Tablets

| Raw material | Amount |
| --- | --- |
| Olive leaf extract (containing 35% oleuropein) | 22 |
| White willow extract | 10 |
| Broccoli sprout extract (containing 2% sulforaphane) | 9 |
| Cellulose | 10 |
| Sucrose fatty acid ester | 3 |
| Reduced maltose starch syrup | Remainder |
| Total | 100 |

Functional food eaten by taking 2 tablets obtained by tableting 200 mg of the above composition at a time. For each intake, the amount of oleuropein is about 30 mg, and the amount of sulforaphane is about 0.7 mg.

Formulation Example 16: Chocolate

| Raw material | Amount |
| --- | --- |
| Olive leaf extract (containing 35% oleuropein) | 0.75 |
| Broccoli sprout extract (containing 2% sulforaphane) | 0.3 |
| Sugar | 35 |
| Cacao butter | 20 |
| Skim milk powder | 1 |
| Emulsifier | 0.05 |
| Cacao mass | Remainder |
| Total | 100 |

Subdivided packs of chocolate containing 20 g of the above composition. For each pack, the amount of oleuropein is 52.2 mg, and the amount of sulforaphane is 1.2 mg.

Formulation Example 17: Chocolate

| Raw material | Amount |
| --- | --- |
| Olive leaf extract (containing 35% oleuropein) | 1 |
| Broccoli sprout extract (containing 2% sulforaphane) | 0.3 |
| Sugar | 35 |
| Cacao butter | 20 |
| Skim milk powder | 1 |
| Emulsifier | 0.05 |
| Cacao mass | Remainder |
| Total | 100 |

Subdivided packs of chocolate containing 20 g of the above composition. For each pack, the amount of oleuropein is 70 mg, and the amount of sulforaphane is 1.2 mg.

Formulation Example 18: Chocolate

| Raw material | Amount |
| --- | --- |
| Olive leaf extract (containing 35% oleuropein) | 1.1 |
| Broccoli sprout extract (containing 2% sulforaphane) | 0.2 |
| Sugar | 35 |
| Cacao butter | 20 |
| Skim milk powder | 1 |
| Emulsifier | 0.05 |
| Cacao mass | Remainder |
| Total | 100 |

Subdivided packs of chocolate containing 20 g of the above composition. For each pack, the amount of oleuropein is 77 mg, and the amount of sulforaphane is 0.8 mg.

Formulation Example 19: Sports Drink Powder

| Raw material | Amount |
| --- | --- |
| Olive leaf extract (containing 10% hydroxytyrosol) | 0.7 |
| Broccoli sprout extract (containing 2% sulforaphane) | 0.07 |
| Fruit juice powder | 17 |
| Sodium chloride | 7 |
| Citric acid | 4 |
| Trisodium citrate | 1.5 |
| Magnesium chloride | 0.03 |
| Potassium chloride | 0.06 |
| Fragrance | 1 |
| Fructose | Remainder |
| Total | 100 |

30 g per pack is dissolved in 500 mL of water for drinking. For each drink, the amount of hydroxytyrosol is 21 mg, and the amount of sulforaphane is about 0.42 mg.

Formulation Example 20: Sports Drink Powder

| Raw material | Amount |
| --- | --- |
| Olive leaf extract (containing 20% hydroxytyrosol) | 0.4 |
| Broccoli sprout extract (containing 2% sulforaphane) | 0.1 |
| Fruit juice powder | 17 |
| Sodium chloride | 7 |
| Citric acid | 4 |
| Trisodium citrate | 1.5 |
| Magnesium chloride | 0.03 |
| Potassium chloride | 0.06 |
| Fragrance | 1 |
| Fructose | Remainder |
| Total | 100 |

30 g per pack is dissolved in 500 mL of water for drinking. For each drink, the amount of hydroxytyrosol is 24 mg, and the amount of sulforaphane is 0.6 mg.

Formulation Example 21: Sports Drink Powder

| Raw material | Amount |
| --- | --- |
| Olive leaf extract (containing 6% hydroxytyrosol) | 1.7 |
| Broccoli sprout extract (containing 2% sulforaphane) | 0.17 |
| Fruit juice powder | 17 |
| Sodium chloride | 7 |
| Citric acid | 4 |
| Trisodium citrate | 1.5 |
| Magnesium chloride | 0.03 |
| Potassium chloride | 0.06 |
| Fragrance | 1 |
| Fructose | Remainder |
| Total | 100 |

30 g per pack is dissolved in 500 mL of water for drinking. For each drink, the amount of hydroxytyrosol is about 31 mg, and the amount of sulforaphane is about 1 mg.

Formulation Example 22: Tea Powder

| Raw material | Amount |
| --- | --- |
| Olive leaf extract (containing 20% hydroxytyrosol) | 2.5 |
| Broccoli sprout extract (containing 2% sulforaphane) | 1.25 |
| Fragrance | 15 |
| Fructose | Remainder |
| Total | 100 |

2 g per pack is dissolved in 150 mL of water for drinking. For each drink, the amount of hydroxytyrosol is 10 mg, and the amount of sulforaphane is 0.5 mg.

Formulation Example 23: Tea Powder

| Raw material | Amount |
| --- | --- |
| Olive leaf extract (containing 10% hydroxytyrosol) | 7.5 |
| Broccoli sprout extract (containing 2% sulforaphane) | 2.5 |
| Fragrance | 15 |
| Fructose | Remainder |
| Total | 100 |

2 g per pack is dissolved in 150 mL of water for drinking. For each drink, the amount of hydroxytyrosol is 15 mg, and the amount of sulforaphane is 1 mg.

Formulation Example 24: Tea Powder

| Raw material | Amount |
| --- | --- |
| Olive leaf extract (containing 20% hydroxytyrosol) | 10 |
| Broccoli sprout extract (containing 2% sulforaphane) | 0.75 |
| Fragrance | 15 |
| Fructose | Remainder |
| Total | 100 |

2 g per pack is dissolved in 150 mL of water for drinking. For each drink, the amount of hydroxytyrosol is 40 mg, and the amount of sulforaphane is 0.3 mg.

Formulation Example 25: Baked Goods

| Raw material | Amount |
| --- | --- |
| Olive leaf extract (containing 6% hydroxytyrosol) | 2.3 |
| Broccoli sprout extract (containing 2% sulforaphane) | 0.1 |
| Reduced starch syrup | 20 |
| Rice oil | 15 |
| Baking powder | 1.5 |
| Salt | 1 |
| Fragrance | 0.3 |
| Water | 15 |
| Soft flour | Remainder |
| Total | 100 |

Subdivided packs each containing 5 baked goods (10 g/piece). For each pack, the amount of hydroxytyrosol is 69 mg, and the amount of sulforaphane is 1 mg.

Formulation Example 26: Baked Goods

| Raw material | Amount |
| --- | --- |
| Olive leaf extract (containing 20% hydroxytyrosol) | 0.9 |
| Broccoli sprout extract (containing 2% sulforaphane) | 0.1 |
| Reduced starch syrup | 20 |
| Rice oil | 15 |
| Baking powder | 1.5 |
| Salt | 1 |
| Fragrance | 0.3 |
| Water | 15 |
| Soft flour | Remainder |
| Total | 100 |

Subdivided packs each containing 5 baked goods (10 g/piece). For each pack, the amount of hydroxytyrosol is 90 mg, and the amount of sulforaphane is 1 mg.

Formulation Example 27: Baked Goods

| Raw material | Amount |
| --- | --- |
| Olive leaf extract (containing 20% hydroxytyrosol) | 1.1 |
| White willow extract | 5 |
| Reduced starch syrup | 20 |
| Rice oil | 15 |
| Baking powder | 1.5 |
| Salt | 1 |
| Fragrance | 0.3 |
| Water | 15 |
| Soft flour | Remainder |
| Total | 100 |

Subdivided packs each containing 5 baked goods (10 g/piece). For each pack, the amount of hydroxytyrosol is 110 mg.

Formulation Example 28: Capsules

| Raw material | Amount |
| --- | --- |
| Olive leaf extract (containing 10% hydroxytyrosol) | 40 |
| Broccoli sprout extract (containing 3% sulforaphane) | 6 |
| Sucrose fatty acid ester | 3 |
| Corn starch | Remainder |
| Total | 100 |

Functional food eaten by taking 3 gelatin hard capsules each containing 150 mg at a time. For each intake, the amount of hydroxytyrosol is 18 mg, and the amount of sulforaphane is about 0.8 mg.

Formulation Example 29: Capsules

| Raw material | Amount |
| --- | --- |
| Olive leaf extract (containing 20% hydroxytyrosol) | 50 |
| Broccoli sprout extract (containing 1% sulforaphane) | 10 |
| Sucrose fatty acid ester | 3 |
| Corn starch | Remainder |
| Total | 100 |

Functional food eaten by taking 3 gelatin hard capsules each containing 150 mg at a time. For each intake, the amount of hydroxytyrosol is 45 mg, and the amount of sulforaphane is 0.45 mg.

Formulation Example 30: Capsules

| Raw material | Amount |
| --- | --- |
| Olive leaf extract (containing 30% hydroxytyrosol) | 60 |
| White willow extract | 5 |
| Sucrose fatty acid ester | 3 |
| Corn starch | Remainder |
| Total | 100 |

Functional food eaten by taking 3 gelatin hard capsules each containing 150 mg at a time. For each intake, the amount of hydroxytyrosol is 81 mg.

Formulation Example 31: Tablets

| Raw material | Amount |
| --- | --- |
| Olive leaf extract (containing 30% hydroxytyrosol) | 50 |
| White willow extract | 5 |
| Cellulose | 10 |
| Sucrose fatty acid ester | 3 |
| Reduced maltose starch syrup | Remainder |
| Total | 100 |

Functional food eaten by taking 3 tablets obtained by tableting 200 mg of the above composition at a time. For each intake, the amount of hydroxytyrosol is 90 mg.

Formulation Example 32: Tablets

| Raw material | Amount |
| --- | --- |
| Olive leaf extract (containing 20% hydroxytyrosol) | 25 |
| Broccoli sprout extract (containing 4% sulforaphane) | 3 |
| Cellulose | 10 |
| Sucrose fatty acid ester | 3 |
| Reduced maltose starch syrup | Remainder |
| Total | 100 |

Functional food eaten by taking 2 tablets obtained by tableting 200 mg of the above composition at a time. For each intake, the amount of hydroxytyrosol is 20 mg, and the amount of sulforaphane is 0.48 mg.

Formulation Example 33: Tablets

| Raw material | Amount |
| --- | --- |
| Olive leaf extract (containing 30% hydroxytyrosol) | 40 |
| White willow extract | 10 |
| Cellulose | 10 |
| Sucrose fatty acid ester | 3 |
| Reduced maltose starch syrup | Remainder |
| Total | 100 |

Functional food eaten by taking 3 tablets obtained by tableting 200 mg of the above composition at a time. For each intake, the amount of hydroxytyrosol is 72 mg.

Formulation Example 34: Chocolate

| Raw material | Amount |
| --- | --- |
| Olive leaf extract (containing 20% hydroxytyrosol) | 0.8 |
| Broccoli sprout extract (containing 2% sulforaphane) | 0.04 |
| Sugar | 35 |
| Cacao butter | 20 |
| Skim milk powder | 1 |
| Emulsifier | 0.05 |
| Cacao mass | Remainder |
| Total | 100 |

Subdivided packs of chocolate containing 20 g of the above composition. For each pack, the amount of hydroxytyrosol is 32 mg, and the amount of sulforaphane is 0.16 mg.

Formulation Example 35: Chocolate

| Raw material | Amount |
| --- | --- |
| Olive leaf extract (containing 20% hydroxytyrosol) | 1 |
| Broccoli sprout extract (containing 2% sulforaphane) | 0.2 |
| Sugar | 35 |
| Cacao butter | 20 |
| Skim milk powder | 1 |
| Emulsifier | 0.05 |
| Cacao mass | Remainder |
| Total | 100 |

Subdivided packs of chocolate containing 20 g of the above composition. For each pack, the amount of hydroxytyrosol is 40 mg, and the amount of sulforaphane is 0.8 mg.

Formulation Example 36: Chocolate

| Raw material | Amount |
| --- | --- |
| Olive leaf extract (containing 20% hydroxytyrosol) | 1.5 |
| Broccoli sprout extract (containing 2% sulforaphane) | 0.1 |

-continued

| Raw material | Amount |
|---|---|
| Sugar | 35 |
| Cacao butter | 20 |
| Skim milk powder | 1 |
| Emulsifier | 0.05 |
| Cacao mass | Remainder |
| Total | 100 |

Subdivided packs of chocolate containing 20 g of the above composition. For each pack, the amount of hydroxytyrosol is 60 mg, and the amount of sulforaphane is 0.4 mg.

The invention claimed is:

1. A method to suppress obesity, comprising administering to a subject in need thereof an effective amount of a composition comprising the following components (A) and (B):
   (A) oleuropein; and
   (B) a sulforaphane compound,
   wherein the amount of component (A) alone contained in the composition does not result in a fat accumulation-suppressing effect, and the amount of component (B) alone contained in the composition does not result in a fat accumulation-suppressing effect.

2. The method according to claim 1, wherein the composition comprises an olive extract comprising the oleuropein, and component (B).

3. The method according to claim 1, wherein the composition is an oral composition.

4. A method to suppress obesity, comprising administering to a subject in need thereof an effective amount of a composition comprising the following components (A) and (B):
   (A) oleuropein; and
   (B) sulforaphane,
   wherein the amount of component (A) alone contained in the composition does not result in a fat accumulation-suppressing effect, and the amount of component (B) alone contained in the composition does not result in a fat accumulation-suppressing effect.

5. The method according to claim 4, wherein the composition comprises an olive extract comprising the (A) oleuropein, and (B) sulforaphane.

6. The method according to claim 1, wherein the composition further comprises at least one ingredient selected from the group consisting of an excipient, a binder, an emulsifier, a sweetener, an acidulant, a fortifier, a dietary fiber, an antioxidant, a seasoning, a fragrance, a coloring agent, a lubricant, and a polysaccharide thickener.

* * * * *